(12) United States Patent
Liang et al.

(10) Patent No.: US 9,603,774 B2
(45) Date of Patent: Mar. 28, 2017

(54) EVIDENCE-BASED ACUPUNCTURE AND MOXIBUSTION MERIDIAN-ACUPOINT TREATING AND DETECTING INSTRUMENT SUPPORTING MULTIPLEXED OUTPUT AND METHOD OF USE THEREOF

(71) Applicants: CHENGDU UNIVERSITY OF TRADITIONAL CHINESE MEDICINE, Chengdu, Sichuan (CN); CHENGDU SUNSHEEN TECHNOLOGY CO., LTD., Chengdu, Sichuan (CN)

(72) Inventors: Fanrong Liang, Sichuan (CN); Hongping Shu, Sichuan (CN); Yulan Ren, Sichuan (CN); Fang Zeng, Sichuan (CN); Ji Li, Sichuan (CN); Taipin Guo, Sichuan (CN); Jie Yang, Sichuan (CN); Liang Chen, Sichuan (CN)

(73) Assignees: CHENGDU UNIVERSITY OF TRADITIONAL CHINESE MEDICINE, Sichuan (CN); CHENGDU SUNSHEEN TECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 14/903,157

(22) PCT Filed: Nov. 9, 2014

(86) PCT No.: PCT/CN2014/090662
§ 371 (c)(1),
(2) Date: Jan. 6, 2016

(87) PCT Pub. No.: WO2015/074498
PCT Pub. Date: May 28, 2015

(65) Prior Publication Data
US 2016/0136044 A1 May 19, 2016

(30) Foreign Application Priority Data

Nov. 21, 2013 (CN) .......................... 2013 1 0587801

(51) Int. Cl.
*A61H 39/00* (2006.01)
*A61H 39/02* (2006.01)
(Continued)

(52) U.S. Cl.
CPC ......... *A61H 39/002* (2013.01); *A61B 5/0532* (2013.01); *A61B 5/4854* (2013.01);
(Continued)

(58) Field of Classification Search
CPC .... A61H 39/002; A61B 5/0532; A61B 5/4854
(Continued)

(56) References Cited

U.S. PATENT DOCUMENTS

| 5,251,637 A * | 10/1993 | Shalvi ................. A61B 5/0532 128/907 |
| 7,321,792 B1 * | 1/2008 | Min ..................... A61H 39/002 128/907 |
| 2004/0230256 A1 | 11/2004 | Lin-Hendel |

FOREIGN PATENT DOCUMENTS

| CN | 2275878 Y | 3/1998 |
| CN | 1775170 A | 5/2006 |

(Continued)

*Primary Examiner* — Eric D. Bertram
(74) *Attorney, Agent, or Firm* — Novick, Kim & Lee, PLLC; Allen Xue

(57) ABSTRACT

A multipath-output-supporting evidence-based acupuncture and moxibustion acupoint therapeutic and detecting instrument and a using method thereof. The therapeutic and detecting instrument comprises a CPU core unit, a communication module, an audio module and a plurality of detecting, diagnosis and treatment circuits. The detecting, diagnosis and treatment circuit comprises an acupoint detecting unit and an acupoint acupuncture and moxibustion unit. The (Continued)

acupoint detecting unit comprises a resistance detecting circuit and an A/D digital converting circuit. The acupoint acupuncture and moxibustion unit comprises a D/A pulse current generating circuit and an amplifying circuit. The CPU core unit comprises an ARM processor, a memory, an auxiliary circuit and an evidence-based acupuncture and moxibustion therapeutic system, and the ARM processor is connected with the evidence-based acupuncture and moxibustion therapeutic system.

6 Claims, 2 Drawing Sheets

(51) Int. Cl.
*A61H 39/06* (2006.01)
*A61B 5/053* (2006.01)
*G06F 19/00* (2011.01)
*A61B 5/00* (2006.01)

(52) U.S. Cl.
CPC ........... *A61B 5/7475* (2013.01); *A61H 39/02* (2013.01); *A61H 39/06* (2013.01); *G06F 19/322* (2013.01); *A61B 5/742* (2013.01); *A61H 2201/5038* (2013.01); *A61H 2201/5043* (2013.01); *A61H 2201/5046* (2013.01); *A61H 2201/5048* (2013.01); *A61H 2201/5097* (2013.01); *G06F 19/3443* (2013.01)

(58) Field of Classification Search
IPC ..................................................... A61H 39/002
See application file for complete search history.

(56) References Cited

FOREIGN PATENT DOCUMENTS

| | | |
|---|---|---|
| CN | 102698371 A | 10/2012 |
| CN | 102902871 A | 1/2013 |
| JP | 2003062034 A | 3/2003 |

* cited by examiner

EVIDENCE-BASED ACUPUNCTURE AND MOXIBUSTION MERIDIAN-ACUPOINT TREATING AND DETECTING INSTRUMENT SUPPORTING MULTIPLEXED OUTPUT AND METHOD OF USE THEREOF

FIELD OF THE INVENTION

This invention relates to a meridian-acupoint treating and detecting instrument, and specifically to an evidence-based acupunctural meridian-acupoint treating and detecting instrument supporting multiplexed output as well as its usage method.

DESCRIPTION OF THE RELATED ART

Medication treatment has side effects on human bodies, and people's drug resistance will increase if too many medicines are took. In case that people has drug resistance, the curative effect of such drug will be very poor even though more of such drug is consumed. Acupuncture treatment can overcome the disadvantages of the medication treatment, and has obvious effects; and also, this therapy is safe and has no toxic side effects. Acupuncture is an unique treatment method of China, and is a treatment skill that can treat an internal illness by external treatment. By means of the conducting functions of meridians and acupuncture points, diseases thoughout the whole body can be treated by applying some kinds of operations. The diagnosis and treatment method of traditional Chinese medicine is clinically used to diagnose the cause of disease, find out the source of the disease, discriminate the properties of the disease, and determine to which meridian and which internal organ the disease belongs, so as to distinguish the disease between exterior and interior, chills and fever, as well as deficiency and excess, thus making diagnoses. Then, a corresponding point-combining prescription is made for treatment. The objectives of preventing and curing diseases are achieved by dredging the meridians, regulating QI-blood, relatively balancing Yin and Yang, and harmonizing the functions of internal organs. Acupuncture treatment is a part of traditional medicine in China, and is also an unique and national medical treating method of China. For thousands of years, acupuncture treatment has made great contributions to keep people healthy, populate the nation and the like, and it still fulfills such tasks nowadays and is trusted by the public.

As the pace of life gets faster and faster, most of young people are busy with their works. No matter whether the work environment is located at a office building or a factory workshop, occupational disease would more or less be caused during work. However, most of young people are busy with their works and have no time to focus on their own healthy problems or focus on the healthy problems of the left-behind elderly. Both the young people and the seniors cannot always timely get treated in the hospital when they don't feel well. On the other hand, nowadays, in acupuncture diagnosis and treatment, detecting physical characteristics of acupoints, locating the acupoints, as well as the acupuncture treatment are all performed according experiences by professional traditional Chinese medical personnel; and unprofessional medical personnel cannot detect and treat by their own, and thus the acupuncture diagnosis and treatment is not so popular up to now. The patient has to go to the clinic in order to get traditional Chinese medicine doctor's diagnosis and cannot perform self-served diagnosis and treatment, which is conflicted with the situation that the patient cannot always timely get treated in the hospital.

The science of acupuncture is a traditional empirical medicine, and acupuncture clinical decision mode that is mainly based on experiences is still predominant to some extents. Since the essential flaw of the science of acupuncture is that it seldom thinks highly of the function and usage of evidences provided by scientific research, further improvement of clinical curative effect of acupuncture and international development of the science of acupuncture are to a certain extent impeded. In recent years, there have been some user-operated acupoint detecting and treating products that are available in the market. From the point of view of identifying acupoint, the location of an acupuncture acupoint is often defined by relative positions of bones, muscles, blood vessels, nerves, lymphs and visceral organs in the human body, and everyone's body figure has many slight differences from others. Even an old and experienced traditional Chinese medicine doctor cannot guarantee the accuracy of locating performed by naked eyes, and existing acupoint detecting and treating products definitely cannot accurately locate the acupoint. As for a user-operated acupoint detecting and treating product, accidents would inevitably happen to a layperson if he/she use the product by himself/herself, thus causing some dangers. In the case of physician, such product can only treat one patient, and cannot treat other patients when such patient is being acupunctured; thus the efficiency is low and it cannot be widely used.

SUMMARY OF THE INVENTION

The Problem to be Solved

A objective of the invention is to overcome the deficiencies of prior art, and to provide a clinical and medical evidence-based acupunctural meridian-acupoint treating and detecting instrument supporting multiplexed output as well as its usage method, which incorporates a technology of detecting meridian acupoint resistance characteristic so as to provide a clinical physician with meridian acupoint specificity resistance parameters for diagnosis reference, supports multiplexed input of acupoint resistance detecting results and multiplexed output of electronic pulse waves, and can simultaneously diagnose and give treatments to multiple patients, thus improving the diagnosis and treatment efficiency of the physician.

Solutions to the Problem

Technical Solutions

The objective of the invention is accomplished by the following technical solutions:

An evidence-based acupunctural meridian-acupoint treating and detecting instrument supporting multiplexed output; the instrument comprises a CPU core unit, a communication module, a human-machine interaction module, a debugging module, an audio module, and a plurality of detecting-diagnosing-treating circuits; the CPU core unit is connected to the detecting-diagnosing-treating circuits respectively via an interface; said detecting-diagnosing-treating circuit comprises an acupoint detecting unit and an acupoint acupuncture unit; the acupoint detecting unit comprises a resistance detecting circuit and an A/D converting digital circuit; the acupoint acupuncture unit comprises a D/A pulse current generating circuit and an amplifying circuit; said CPU core unit comprises an ARM processor, a memory, an auxiliary circuit and an evidence-based acupunctural treatment system;

output of the resistance detecting circuit is connected to the ARM processor via the A/D converting digital circuit; outputs of the ARM processor are respectively connected to the auxiliary circuit, the audio module and the D/A pulse current generating circuit; output of D/A pulse current generating circuit is connected to the amplifying circuit; output of the amplifying circuit is connected to the acupoint acupuncturing device; the ARM processor is also respectively connected to the communication module, the memory, the evidence-based acupunctural treatment system, the human-machine interaction module and the debugging module;

said evidence-based acupunctural treatment system comprises the following functional modules:

a system parameter setting module for setting instrument parameters, including acoustic adjustment of the audio module, brightness adjustment of a screen and setting an acupoint standard resistance;

a system updating module for upgrading the system through network when a new version is available for the system, wherein the contents of upgrading include updating general-purpose prescriptions;

a traditional Chinese medicine meridian acupoint knowledge query module for inquiring the names of human body's meridians and corresponding acupoints, as well as meridian acupoint locations and related knowledges; this module comprises a human body's meridian knowledge query module and a human body's acupoint knowledge query module;

a general-purpose prescription management module that mainly keeps evidence-based evaluations about the specificity of the meridians and acupoints, as well as evidence-based prescriptions and data mining prescriptions from a clinical decision platform; this module keeps traditional Chinese medicine symptoms and corresponding acupuncture prescriptions, and regularly updates them through the communication module;

an electronic patient record module for recording a history of acupoint detecting results and acupuncture prescriptions of each patient;

a user-defined prescription module that mainly keeps diagnostic prescriptions of physicians; the instrument is capable of conducting acupuncture treatment with respect to the symptoms according to the diagnostic prescriptions of physicians;

an acupoint deficiency/excess detecting module for determining the resistance characteristic of a acupoint according to the acupoint resistance detected by the resistance detecting circuit; and this module decides that the acupoint is deficient when the detected acupoint resistance value is smaller than a standard resistance value, and otherwise decides that the acupoint is excess;

a treatment module for determining electronic pulse wave parameters of acupuncture according to the decision made by the acupoint deficiency/excess detecting module and the diagnostic prescription to be conducted by the user-defined prescription module; wherein the electronic acupuncture pulse waveform could be continuous wave, dilatational wave and intermittent wave;

a management module for managing detecting results of acupoint detecting units uploaded via individual interfaces, and transferring acupuncture prescriptions of patients to individual corresponding acupoint acupuncture units.

Said communication module comprises WIFI or GPRS or Internet.

Said human-machine interaction module comprises buttons and a touch screen.

Said audio module comprises an audio conversion circuit and a loudspeaker; wherein, input of the audio conversion circuit is connected to the ARM processor, and output of the audio conversion circuit is connected to the loudspeaker.

A method using the evidence-based acupunctural meridian-acupoint treating and detecting instrument supporting multiplexed output, and the method comprises following steps:

S1: a user powers up the instrument and logs in, and the meridian-acupoint treating and detecting instrument detects whether any update is available, and inquires the user whether or not to make update if update is available; the instrument needs to be restarted after being updated; also, a detecting-diagnosing-treating function is enabled if no update is available;

S2: the resistance detecting circuit performs resistance detection on an acupoint of a patient, and the detected resistance value is subjected to an A/D digital conversion and then uploaded to the management module; the ARM processor determines the resistance characteristic of the acupoint; the acupuncture operation needs not be performed if the acupoint is decided to be excess, and the acupuncture operation needs to be performed if the acupoint is decided to be deficient;

S3: the user selects a general-purpose prescription therapy or a user-defined prescription therapy; if a general-purpose prescription therapy is selected, the user is prompted to input therapy parameters, and the general-purpose prescription management module prescribes an acupuncture prescription according to the parameters; if a user-defined prescription therapy is selected, the physician prescribes an acupuncture prescription according to the parameters detected from the patient, and delivers the prescribed acupuncture prescription to the treatment module;

S4: the treatment module determines electronic pulse wave parameters of an acupoint acupuncture circuit according to the acupuncture prescription, and delivers them to the management module;

S5: the management module delivers individual determined electronic pulse wave parameters respectively to D/A pulse current generating circuits at corresponding interfaces, so as to generate pulse waves in order to acupuncture the acupoint.

Said usage method further comprises a step of inquiring traditional Chinese medicine meridian acupuncture point knowledge, so that the user can inquire knowledges related to human body's meridians and acupoints at any time when using the instrument.

Said usage method further comprises a displaying step and a voice broadcast step; said displaying step displays in a rolling fashion detected resistance values of individual interfaces, treating steps, electronic pulse wave parameters, and tips in the form of pictures or texts; said voice broadcast step reminds the user of acupuncture parameter settings, acupuncture acupoints and acupuncture time by voices.

The resistance detection in said step S2 employs an AC four electrode method.

Beneficial Effects of the Invention

Beneficial Effects

The beneficial effects of the invention includes:

1. It teaches a technology of detecting meridian acupoint resistance characteristic so as to provide a clinical physician with meridian acupoint specificity resistance parameters for diagnosis reference, is provided with multiple interfaces for the detecting-diagnosing-treating circuits, supports multiplexed input of acupoint resistance detecting results and multiplexed output of electronic pulse waves, can simultaneously diagnose and give treatments to multiple patients so as to improve the diagnosis and treatment efficiency of the physician, and can be clinically and medically applied;

2. It is provided with a traditional Chinese medicine meridian acupoint knowledge query module, a general-purpose prescription management module, a user-defined prescription module and an electronic patient record module and so on, provides platform-based and evidence-based support for diagnosis and policy decision, and provides clinical physicians with evidence reference; and the physician can register on a well-established evidence-based acupunctural clinical decision network platform, inquires evidence-based acupunctural clinical prescriptions based on symptoms of the patient, and conduct remote expert consultation;

3. It is capable of adjusting pulse therapy parameters with high sensitivity in a visible way, and is capable of displaying in a rolling fashion detected resistance values of individual interfaces, treating steps, electronic pulse wave parameters, and tips in the form of pictures or texts shown during inquiring traditional Chinese medicine meridian acupuncture point knowledge, making clinical treatment more convenient.

DETAILED DESCRIPTION OF THE PREFERRED EMBODIMENTS

In the following, technical solutions of this invention are further described in connection of the figures. However, the contents sought to be protected by the present invention is not limited thereto.

Figure 1:
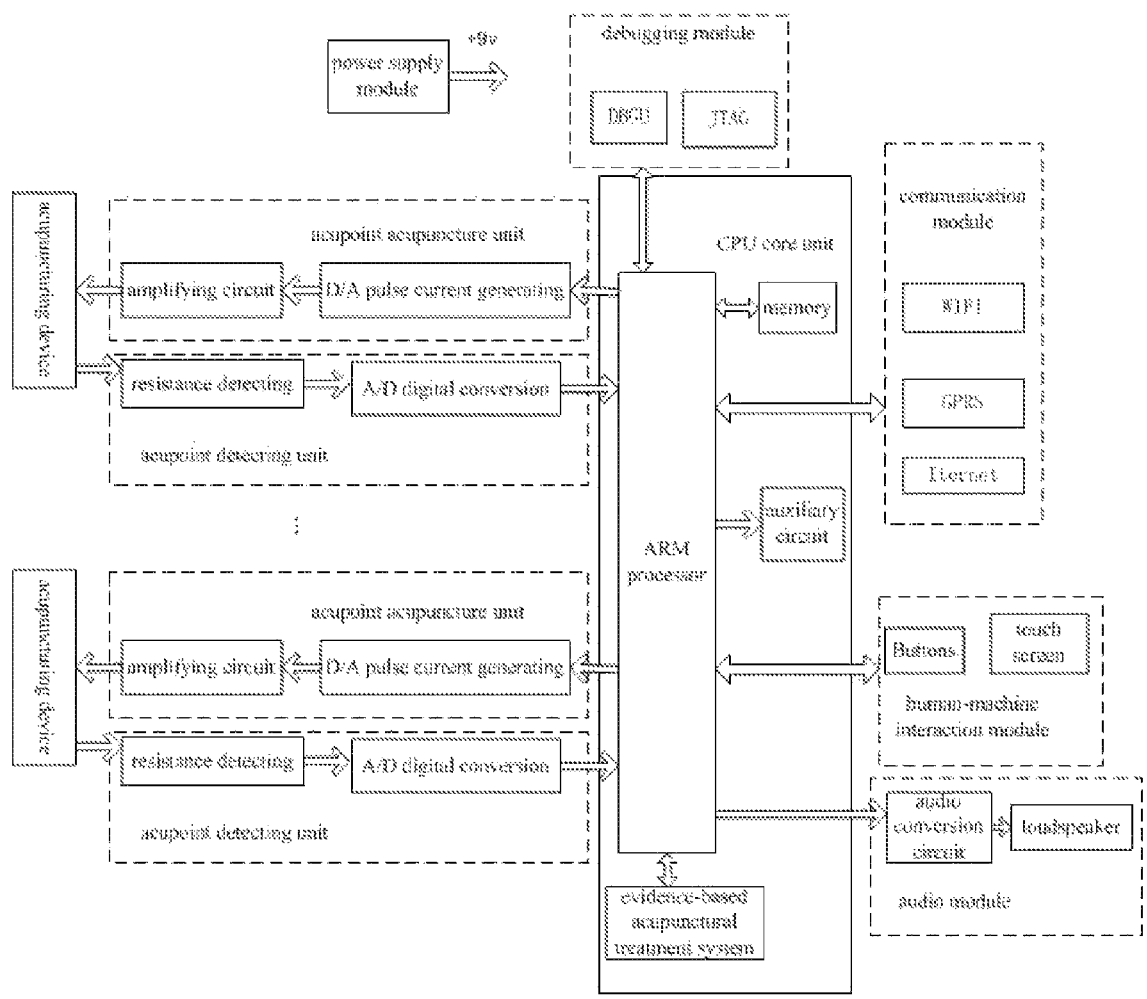
FIG. 1 is a schematic diagram of system structure of the invention.

As shown in FIG. 1, an evidence-based acupunctural meridian-acupoint treating and detecting instrument supporting multiplexed output comprises a CPU core unit, a communication module, a human-machine interaction module, a debugging module, an audio module, and a plurality of detecting-diagnosing-treating circuits; the CPU core unit is connected to the detecting-diagnosing-treating circuits respectively via an interface; said detecting-diagnosing-treating circuit comprises an acupoint detecting unit and an acupoint acupuncture unit; the acupoint detecting unit comprises a resistance detecting circuit and an A/D converting digital circuit; the acupoint acupuncture unit comprises a D/A pulse current generating circuit and an amplifying circuit; said CPU core unit comprises an ARM processor, a memory, an auxiliary circuit and an evidence-based acupunctural treatment system.

The output of the resistance detecting circuit is connected to the ARM processor via the A/D converting digital circuit; outputs of the ARM processor are respectively connected to the auxiliary circuit, the audio module and the D/A pulse current generating circuit; the output of D/A pulse current generating circuit is connected to the amplifying circuit; the output of the amplifying circuit is connected to the acupoint acupuncturing device; the ARM processor is also respectively connected to the communication module, the memory, the evidence-based acupunctural treatment system, the human-machine interaction module and the debugging module.

Figure 2:
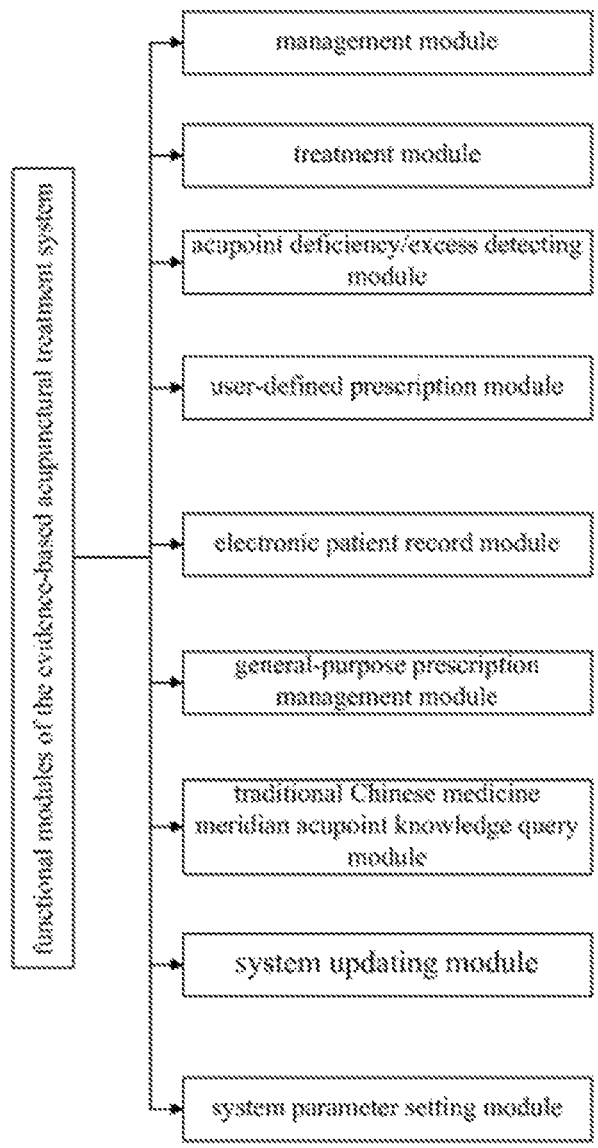
FIG. 2 is a structure diagram of functional modules of the evidence-based acupunctural treatment system of the invention.

As shown in FIG. 2, said evidence-based acupunctural treatment system comprises the following functional modules:

a system parameter setting module for setting instrument parameters, including acoustic adjustment of the audio module, brightness adjustment of a screen and setting an acupoint standard resistance;

a system updating module for upgrading the system through network when a new version is available for the system, wherein the contents of upgrading include updating general-purpose prescriptions;

a traditional Chinese medicine meridian acupoint knowledge query module for inquiring the names of human body's meridians and corresponding acupoints, as well as meridian acupoint locations and related knowledges; this module comprises a human body's meridian knowledge query module and a human body's acupoint knowledge query module; a traditional Chinese medicine acupunctural physician can inquire descriptions about human body's meridians and acupoints as well as specific locations that meridians and acupoints lie within human body via this module;

a general-purpose prescription management module that mainly keeps evidence-based evaluations about the specificity of the meridians and acupoints, as well as evidence-based prescriptions and data mining prescriptions from a clinical decision platform; this module keeps traditional Chinese medicine symptoms and corresponding acupuncture prescriptions, and regularly updates them through the communication module;

an electronic patient record module for recording a history of acupoint detecting results and acupuncture prescriptions of each patient;

a user-defined prescription module that mainly keeps diagnostic prescriptions of physicians; the instrument is capable of conducting acupuncture treatment with respect to the symptoms according to the diagnostic prescriptions of physicians;

an acupoint deficiency/excess detecting module: an acupoint has a response function and an effect function; the response function is a direct embodiment of relating meridian acupoint with diseased region, and is the basis of the effect function; an acupoint body surface resistance is a commonly used objective indicator during meridian acupointrepercussion study. The acupoint deficiency/excess detecting module is used for determining the resistance characteristic of an acupoint according to the acupoint resistance detected by the resistance detecting circuit; and this module decides that the acupoint is deficient when the detected acupoint resistance value is smaller than a standard resistance value, and otherwise decides that the acupoint is excess;

a treatment module for determining electronic pulse wave parameters of acupuncture according to the decision made by the acupoint deficiency/excess detecting module and the diagnostic prescription to be conducted by the user-defined prescription module; wherein the electronic acupuncture pulse waveform can be continuous wave, dilatational wave and intermittent wave; the details are as follows:

continuous wave: one of the composite waves outputted by an electric acupuncture apparatus, constituted by simply repeating basic pulse waves, with no pause therein, and with a frequency that is consecutive and adjustable. The continuous wave with a frequency lower than 30 HZ is called as rarefaction wave, and the continuous wave with a frequency higher than 30 HZ is called as condensational wave. A rarefaction wave may cause muscle contractions, generates intensive vibratory sense, enhances the tensile force of muscles and ligament, adjusts the systolic and diastolic function of blood vessel, improves blood circulation, promotes the recovery of nerve-muscle function, and has good therapeutic effect on nerve-muscle paralysis disease; while, the condensational wave has weak vibratory sense, acts on some achy regions of the body surface, and has an effect of immediate analgesia. The adjustable frequencies of all the continuous waves include 2 HZ, 5 HZ, 10 HZ, 15 HZ, 30 HZ, 50 HZ and 100 HZ.

dilatational wave: a composite wave outputted by an electric acupuncture apparatus and with frequency preriodically becoming faster and slower, wherein the rarefaction wave and the condensational wave alternately emerged, and the duration of each wave is about 1.5S, uneasy to cause adaptation reaction to tissues, and normally used for acupuncture anaesthesia. It is a current alternately rarefactional and condensational, can cause the muscle relax and contract rhythmically, can strengthen blood circulation and lymph circulation, can adjust nutrient metabolism of the tissues, and has certain curative effect on some diseases such as soft tissue injury, lumbodorsal fascia strains, and some nerve-muscle paralyzations. The adjustable frequencies include alternately emerged 2 HZ and 15 HZ, alternately emerged 2 HZ and 30 HZ, alternately emerged 2 HZ and 50 HZ, as well as alternately emerged 2 HZ and 100 HZ.

intermittent wave: a composite wave that periodically intermittent, also a sequence of pulse waves obtained by performing rectangular pulse modulation on continuous wave. The adjustable frequencies include 2 HZ, 5 HZ, 10 HZ, 15 HZ, 30 HZ, 50 HZ and 100 HZ.

a management module for managing the detecting results of acupoint detecting units uploaded via individual interfaces, and transferring acupuncture prescriptions of patients to individual corresponding acupoint acupuncture units.

Said communication module comprises WIFI or GPRS or Internet.

Said human-machine interaction module comprises buttons and a touch screen.

Said audio module comprises an audio conversion circuit and a loudspeaker; wherein, the input of the audio conversion circuit is connected to the ARM processor, and the output of the audio conversion circuit is connected to the loudspeaker.

A method of the evidence-based acupunctural meridian-acupoint treating and detecting instrument supporting multiplexed output comprises following steps:

S1: a user powers up the instrument and logs in, and the meridian-acupoint treating and detecting instrument detects whether any update is available, and inquires the user whether or not to make update if update is available; the instrument needs to be restarted after being updated; also, a detecting-diagnosing-treating function is enabled if no update is available;

S2: the resistance detecting circuit performs resistance detection on an acupoint of a patient, and the detected resistance value is subjected to an A/D digital conversion and is then uploaded to the management module; the ARM processor determines the resistance characteristic of the acupoint; the acupuncture operation has no need to be performed if the acupoint is decided to be excess, and the acupuncture operation needs to be performed if the acupoint is decided to be deficient;

S3: the user selects a general-purpose prescription therapy or a user-defined prescription therapy; if a general-purpose prescription therapy is selected, the user is prompted to input therapy parameters, and the general-purpose prescription management module prescribes an acupuncture prescription according to the parameters; if a user-defined prescription therapy is selected, the physician prescribes an acupuncture prescription according to the parameters detected from the patient, and delivers the prescribed acupuncture prescription to the treatment module;

S4: the treatment module determines electronic pulse wave parameters of an acupoint acupuncture circuit according to the acupuncture prescription, and delivers them to the management module;

S5: the management module delivers individual determined electronic pulse wave parameters respectively to D/A pulse current generating circuits at corresponding interfaces, so as to generate pulse waves in order to acupuncture the acupoint.

Said method further comprises a step of inquiring traditional Chinese medicine meridian acupuncture point knowledge, so that the user can inquire knowledges related to human body's meridians and acupoints at any time when using the instrument.

Said method further comprises a displaying step and a voice broadcast step; said displaying step displays in a rolling fashion detected resistance values of individual interfaces, treating steps, electronic pulse wave parameters, and tips in the form of pictures or texts; said voice broadcast step reminds the user of acupuncture parameter settings, acupuncture acupoints and acupuncture time by voices.

The resistance detection in said step S2 employs an AC four electrode method.

The meridian-acupoint treating and detecting instrument of the invention uses a voltage module that provides output at +9V, and supplies power for other modules of the meridian-acupoint treating and detecting instrument.

The CPU core module carries a corresponding embedded operating system (android 4.0 system) and is a core device of the meridian acupoint physiotherapy instrument, which controls other modules through peripheral interfaces, and uses the embedded operating system and designed embedded application system to enable the instrument management, data management, acupoint diction and electronic acupuncture control. By means of the debugging module, an embedded system and driver can be burnt-in and written into the hardware, and the debugging module comprises a DBGU debugging unit and a JTAG debugging unit, and is a circuit designed for hardware programming.

The invention claimed is:

1. An evidence-based acupunctural meridian-acupoint treating and detecting instrument supporting multiplexed output, comprising:
a CPU core unit, a communication module, a human-machine interaction module, a debugging module, an audio module, and a plurality of detecting-diagnosing-treating circuits,
wherein the CPU core unit is connected to each of the plurality of detecting-diagnosing-treating circuits,
wherein each of the plurality of detecting-diagnosing-treating circuits comprises an acupoint detecting unit and an acupoint acupuncture unit; the acupoint detecting unit comprises a resistance detecting circuit and an A/D converting digital circuit; the acupoint acupuncture unit comprises a D/A pulse current generating circuit and an amplifying circuit; said CPU core unit comprises an ARM processor, a memory, an auxiliary circuit and an evidence-based acupunctural treatment system;

wherein the resistance detecting circuit is connected to the ARM processor via the A/D converting digital circuit; the D/A pulse current generating circuit is connected to the amplifying circuit; the amplifying circuit is connected to the acupoint acupuncturing device; the ARM processor is connected to the auxiliary circuit, the audio module, the D/A pulse current generating circuit, the communication module, the memory, the evidence-based acupunctural treatment system, and the human-machine interaction module, and wherein the resistance detecting circuit measures an acupoint resistance, when the acupoint resistance is smaller than a predetermined resistance value, the D/A pluse current generating circuit generates pulse waves to the acupoint.

2. The evidence-based acupunctural meridian-acupoint treating and detecting instrument supporting multiplexed output according to claim 1, wherein said human-machine interaction module comprises buttons and a touch screen.

3. The evidence-based acupunctural meridian-acupoint treating and detecting instrument supporting multiplexed output according to claim 1, wherein said audio module comprises an audio conversion circuit and a loudspeaker, and the audio conversion circuit is connected to the ARM processor, and the loudspeaker.

4. The evidence-based acupunctural meridian-acupoint treating and detecting instrument supporting multiplexed output according to claim 1, wherein the pulse waves are continuous waves, dilatational waves, or intermittent waves.

5. The evidence-based acupunctural meridian-acupoint treating and detecting instrument supporting multiplexed output according to claim 1, wherein the communication module is coupled to the CPU core unit and comprises connections via WIFI, GPRS, and Internet.

6. The evidence-based acupunctural meridian-acupoint treating and detecting instrument supporting multiplexed output according to claim 1, wherein the D/A pluse current generating circuit automatically generates pulse waves to the acupoint when the acupoint resistance is smaller than the predetermined resistance value.

* * * * *